(12) United States Patent
Son

(10) Patent No.: US 9,883,846 B2
(45) Date of Patent: Feb. 6, 2018

(54) MAMMOGRAPHY DEVICE

(71) Applicant: GENERAL ELECTRIC COMPANY, Schenectady, NY (US)

(72) Inventor: Min Ho Son, Hwaseong (KR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 125 days.

(21) Appl. No.: 14/781,023

(22) PCT Filed: Sep. 30, 2013

(86) PCT No.: PCT/KR2013/008767
§ 371 (c)(1),
(2) Date: Sep. 28, 2015

(87) PCT Pub. No.: WO2014/157795
PCT Pub. Date: Oct. 2, 2014

(65) Prior Publication Data
US 2016/0045178 A1  Feb. 18, 2016

(30) Foreign Application Priority Data

Mar. 29, 2013 (KR) .................. 10-2013-0034405

(51) Int. Cl.
*A61B 6/00* (2006.01)
*A61B 6/04* (2006.01)
*A61B 6/03* (2006.01)

(52) U.S. Cl.
CPC ............... *A61B 6/502* (2013.01); *A61B 6/03* (2013.01); *A61B 6/04* (2013.01); *A61B 6/0407* (2013.01);
(Continued)

(58) Field of Classification Search
CPC ....... A61B 6/04; A61B 6/0407; A61B 6/0414; A61B 6/0421; A61B 6/4435; A61B 6/4441; A61B 6/502
(Continued)

(56) References Cited

U.S. PATENT DOCUMENTS 5,029,193 A   7/1991   Saffer
5,050,197 A   9/1991   Virta et al.
(Continued)

FOREIGN PATENT DOCUMENTS

EP   0 370 089 A1   5/1990
JP   H02-504353 A   12/1990
(Continued)

OTHER PUBLICATIONS

International Search Report for PCT/KR2013/008767 filed on Sep. 30, 2013.
(Continued)

*Primary Examiner* — Allen C. Ho

(57) ABSTRACT

Disclosed herein is a mammography device for X-ray photographing an object to be inspected. The mammography device includes: a generator irradiating an X-ray; a support part for an object to be inspected including a detector positioned to face the generator; and a pressing pad moving between the generator and the support part for an object to be inspected to press the object to be inspected, wherein at least one of the support part for an object to be inspected and the pressing pad is rotatably installed at one side of the mammography device, and in a pressing initial state of the object to be inspected, at least one of the support part for an object to be inspected and the pressing pad that is rotatably installed is configured so that a front end portion thereof toward a subject is elastically deflected to a position inclined toward the object to be inspected.

8 Claims, 3 Drawing Sheets

(52) U.S. Cl.
CPC .......... *A61B 6/0414* (2013.01); *A61B 6/0421* (2013.01); *A61B 6/4435* (2013.01); *A61B 6/4441* (2013.01)

(58) Field of Classification Search
USPC .......................................... 378/37, 208, 209
See application file for complete search history.

(56) References Cited

U.S. PATENT DOCUMENTS

| | | | |
|---|---|---|---|
| 5,506,877 A | 4/1996 | Niklason et al. | |
| 5,706,327 A * | 1/1998 | Adamkowski | A61B 6/0414 378/208 |
| 5,851,180 A * | 12/1998 | Crosby | A61B 6/0414 378/37 |
| 6,577,702 B1 * | 6/2003 | Lebovic | A61B 6/0414 378/208 |
| 6,577,703 B2 * | 6/2003 | Lindström | A61B 6/502 378/208 |
| 6,999,553 B2 * | 2/2006 | Livingston | A61B 6/502 378/177 |
| 6,999,554 B2 * | 2/2006 | Mertelmeier | A61B 6/0414 378/196 |
| 7,327,826 B2 * | 2/2008 | Hanke | A61B 6/06 378/155 |
| 7,545,908 B2 * | 6/2009 | Hemmendorff | A61B 6/502 378/205 |
| 7,639,778 B2 * | 12/2009 | Kashiwagi | A61B 6/0414 378/180 |
| 7,693,255 B2 * | 4/2010 | Patoureaux | A61B 6/0414 378/195 |
| 7,756,246 B2 * | 7/2010 | Mikami | A61B 6/0414 378/37 |
| 7,835,490 B2 * | 11/2010 | Ramsauer | A61B 6/0414 378/197 |
| 7,885,379 B2 * | 2/2011 | Meer | A61B 6/502 378/37 |
| 7,916,832 B2 * | 3/2011 | Hara | A61B 6/4494 378/20 |
| 8,031,834 B2 * | 10/2011 | Ludwig | A61B 6/025 378/22 |
| 8,553,837 B2 * | 10/2013 | Johansson | A61B 6/025 378/22 |
| 8,594,275 B2 * | 11/2013 | Matsuura | A61B 6/0414 378/208 |
| 8,611,491 B2 * | 12/2013 | Holler | A61B 6/0414 378/206 |
| 8,787,522 B2 * | 7/2014 | Smith | A61B 6/025 378/20 |
| 8,792,617 B2 * | 7/2014 | Baetz | A61B 6/4035 378/16 |
| 8,848,865 B2 * | 9/2014 | Nakayama | A61B 6/0414 378/37 |
| 9,036,774 B2 * | 5/2015 | Otokuni | A61B 6/0414 378/208 |
| 9,060,739 B2 * | 6/2015 | Kim | A61B 6/035 |
| 9,226,724 B2 * | 1/2016 | Kuwabara | A61B 6/022 |
| 9,282,942 B2 * | 3/2016 | Mertelmeier | A61B 6/502 |
| 9,339,244 B2 * | 5/2016 | Takata | A61B 6/544 |
| 9,468,411 B2 * | 10/2016 | Muller | A61B 6/025 |
| 9,492,128 B2 * | 11/2016 | Lee | A61B 6/0414 |
| 9,517,038 B2 * | 12/2016 | Williams | A61B 6/0414 |
| 9,532,752 B2 * | 1/2017 | Goossen | A61B 6/0414 |
| 9,636,073 B2 * | 5/2017 | Evans | A61B 6/502 |
| 2002/0061090 A1 | 5/2002 | Lindstrom et al. | |
| 2005/0008117 A1 | 1/2005 | Livingston | |
| 2008/0080668 A1 | 4/2008 | Kashiwagi | |
| 2011/0228902 A1 | 9/2011 | Virta | |

FOREIGN PATENT DOCUMENTS

| | | |
|---|---|---|
| JP | H03-018811 U | 2/1991 |
| JP | H03-086154 A | 4/1991 |
| JP | H05-076409 U | 10/1993 |
| JP | 2004-33790 A | 2/2004 |
| JP | 2006-212427 A | 8/2006 |
| JP | 2007-229269 A | 9/2007 |
| JP | 2010-179030 A | 8/2010 |
| WO | WO 89/11248 A1 | 11/1989 |

OTHER PUBLICATIONS

Extended European Search Report for European Patent Application No. 13880062.8 dated Feb. 26, 2016.

* cited by examiner

[Fig. 1]
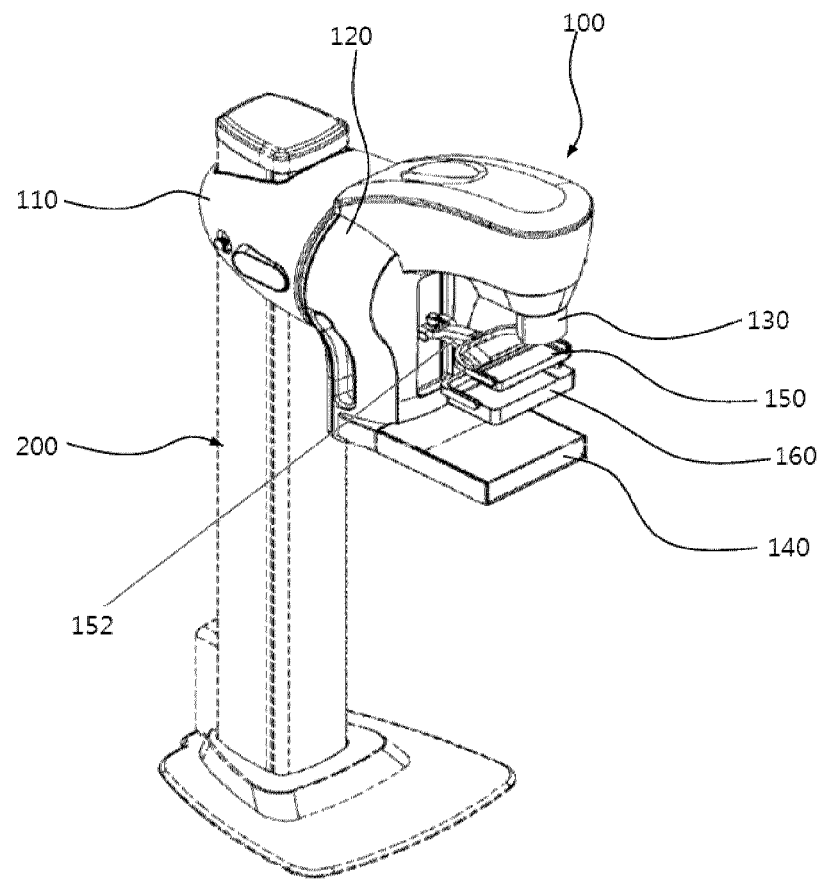
[Fig. 2A]
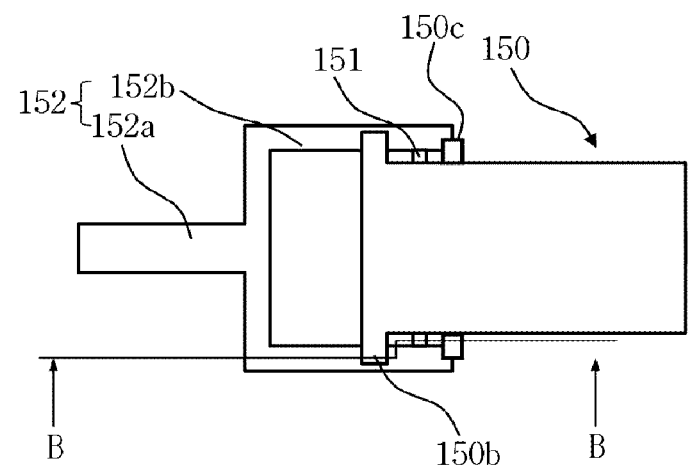

[Fig. 2B]
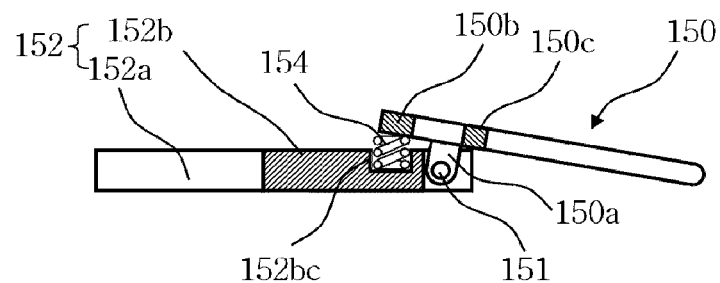
[Fig. 3]
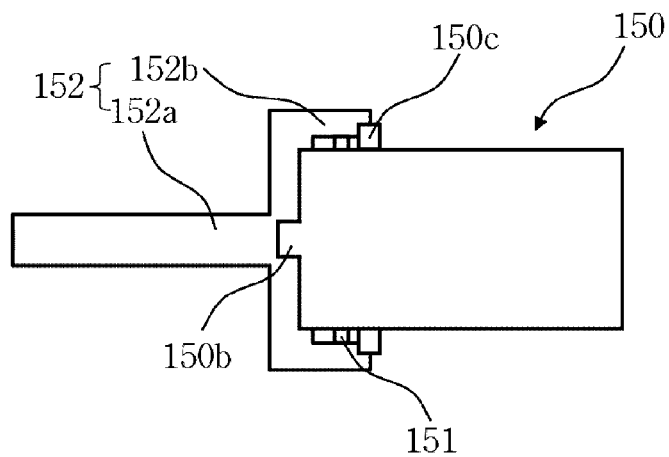
[Fig. 4A]
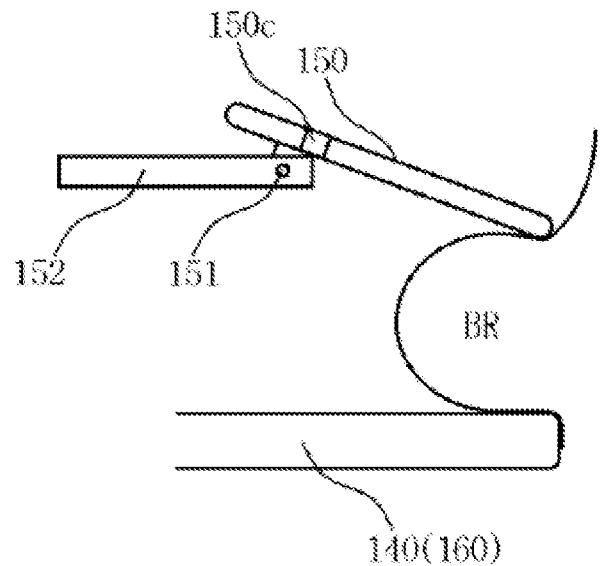

[Fig. 4B]
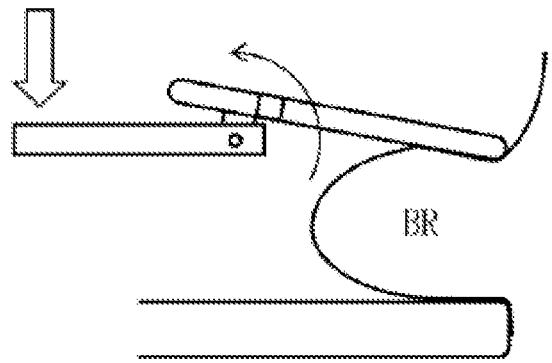
[Fig. 4C]
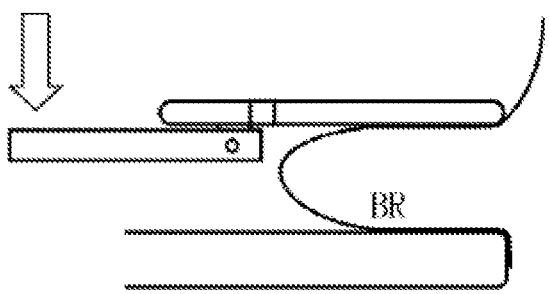
[Fig. 5]
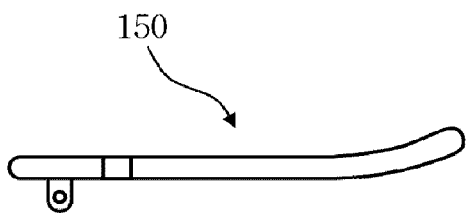
[Fig. 6]
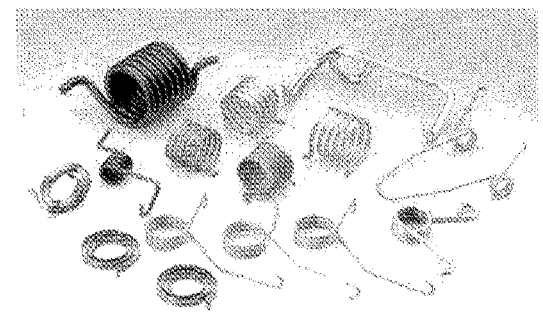

MAMMOGRAPHY DEVICE

TECHNICAL FIELD

The present invention relates to a mammography device for X-ray photographing an object to be inspected, and more particularly, to a mammography device capable of alleviating pain at the time of pressing an object to be inspected by a pressing pad.

The present invention is derived from research performed as a part of nano-material based multi X-ray source and tomography image system technology development of the Ministry of Knowledge Economy [Project Management Number: 10037414, Project Name: Nano-material Based Multi X-ray Source and Tomography Image System Technology Development].

BACKGROUND ART

This application is based on and claims the benefit of priority to Korean Patent Application No. 10-2013-0034405, filed on Mar. 29, 2013 in the Korean Intellectual Property Office, the disclosure of which is incorporated herein in its entirety by reference.

An X-ray generally indicates a short wavelength electromagnetic wave having a wavelength of 0.01 nm to 10 nm and a frequency of $30 \times 10^{15}$ Hz to $30 \times 10^{18}$ Hz. X-ray photographing is one of radiographies of projecting and displaying an inner portion of an object to be inspected by high penetration power of the X-ray. As well-known, the X-ray involves an attenuation phenomenon depending on a material, a density, and a thickness of an object, such as Compton scattering, a photoelectric effect, or the like, during a process in which it is transmitted through the object. Therefore, the X-ray photographing projects and displays the inner portion of the object to be inspected on the basis of an attenuation amount of the X-ray accumulated during a process in which the X-ray passes through the object to be inspected. To this end, a dedicated X-ray system is used.

Recently, an X-ray image technology has been rapidly evolved as a digital X-ray image technology having various advantages such as a relatively high resolution, a wide dynamic area, easy generation of an electrical signal, simple processing and storing of data, and the like, instead of a traditional analog scheme using a film while being grafted onto a semiconductor field. A digital based image technology strongly reflects a clinically environmental demand such as an early diagnosis of a disease on the basis of excellent diagnosis ability of a digital image.

Therefore, a "digital mammography", which is a breast dedicated X-ray photographing technology capable of detecting a lesion and micro-calcification for detection and an early diagnosis of a breast cancer by representing an internal structure of the breast corresponding to an object to be inspected as a high resolution image, using unique biological tissue contrast capability of the X-ray, has been introduced. The digital mammography has been rapidly spread due to unique characteristics such as image enlargement, a decrease in the number of times of photographing, an increase in a resolution, and minimization of exposure through adjustment of a luminance and a contrast ratio together with various advantages of the digital X-ray image technology.

A general mammography device mainly includes a support column having a lower end portion fixed to a bottom and having a vertical column shape and a C-arm or a device body installed on the support column so as to ascend or descend in a vertical direction and generally having a C shape or a shape similar to the C shape in which a central portion thereof is configured to be rotatable with respect to a horizontal axis. A generator irradiating an X-ray toward a lower end portion of the device body is mounted at an upper end portion of the device body, and a detector facing the generator is mounted at the lower end portion of the device body. A pressing pad that vertically and linearly reciprocates along an inner surface of the device body is installed between the generator and the detector.

In the mammography device as described above, when a subject is in a standing or sitting state at a photographing position, the device body ascends or descends and rotates with respect to the support column, such that a height and an angle of the device body are adjusted so that a breast of the subject is put at a target position on the detector. Then, the pressing pad moves toward the detector to press the breast. In this state, the generator irradiates the X-ray toward the breast and the detector, and the detector positioned behind the breast receives the X-ray passing through the breast to obtain an image.

That is, the detector generates an electric signal for each position that is in proportion to an amount of incident X-ray, and reads the electrical signal and position information and processes the read electrical signal and position information by an image processing algorithm, thereby making it possible to obtain an X-ray image of the breast for a corresponding angle. Then, the above-process is repeated while rotating the generator and the detector with the breast interposed therebetween, whereby the mammography device may obtain high resolution images for the breast of the subject at various mediolateral oblique view angles.

In a general mammography device having the above-mentioned photographing principle, a critical driving mechanical for minimizing discomfort of the subject and obtaining a high quality X-ray image is a pressing operation of the pressing pad and ascending or descending and rotating operations of the device body. Particularly, since the pressing pad applies direct pressure to the breast at the time of X-ray photographing, it is directly associated with pain and discomfort felt by the subject, and since the device body determines an accurate photographing position through ascent or descent and rotation, it is directly associated with quality of the X-ray image.

Here, the pressing pad presses the breast in order to photograph the breast in a state in which the breast is pressed for the purpose of separating a lump (a lesion or a portion at which the possibility of micro-calcification is high) looking like being overlapped with a mammary gland, or the like, from the mammary gland.

However, the pressing by the pressing pad, which is the largest pain felt by the subject, causes large discomfort. Further, when the subject moves due to the pain and the discomfort caused by the pressing of the pressing pad, the breast is out of a photographing position, such that an accurate X-ray image may not be obtained. Particularly, the pain due to the pressing of the pressing pad is mainly felt particularly at a distal portion (a portion adjacent to a nipple) of the breast of the subject, and the discomfort is further increased.

DISCLOSURE

Technical Problem

Therefore, the present invention has been made to solve the above-mentioned problems of the related art. An object of the present invention is to provide a mammography device capable of providing comfort to a subject by removing or minimizing pain or discomfort applied to the subject at the time of pressing an object to be inspected by a pressing pad and providing a high photographing accuracy.

Technical Solution

According to an aspect of the present invention, there is provided a mammography device including: a generator irradiating an X-ray; a support part for an object to be inspected including a detector positioned to face the generator; and a pressing pad moving between the generator and the support part for an object to be inspected to press the object to be inspected, wherein at least one of the support part for an object to be inspected and the pressing pad is rotatably installed at one side of the mammography device, and in a pressing initial state of the object to be inspected, at least one of the support part for an object to be inspected and the pressing pad that is rotatably installed is configured so that a front end portion thereof toward a subject is elastically deflected to a position inclined toward the object to be inspected.

In a pressing completion state of the object to be inspected, the support part for an object to be inspected and the pressing pad may be configured in parallel with each other.

The front end portion of at least one of the support part for an object to be inspected and the pressing pad that is rotatably installed may have a round shape at at least an edge thereof contacting the object to be inspected.

The front end portion of at least one of the support part for an object to be inspected and the pressing pad that is rotatably installed may have a shape in which the front end portion is bent in a direction in which the front end portion becomes distant from the object to be inspected.

The mammography device may further include: an elastic member providing elasticity to at least one of the support part for an object to be inspected and the pressing pad that is rotatably installed when at least one of the support part for an object to be inspected and the pressing pad that is rotatably installed rotates between an inclined position in the pressing initial state of the object to be inspected and a parallel position in the pressing completion state of the object to be inspected; and a stopper limiting an angle of the rotation.

The mammography device may further include a pressing pad support part moving between the generator and the support part for an object to be inspected, wherein the pressing pad is rotatably connected to the pressing pad support part.

The elastic member may be at least one of a coil spring interposed between the pressing pad and a pressing pad support part and a twisting spring installed on a hinge shaft rotatably connecting the pressing pad to the pressing pad support part.

Advantageous Effects

In the mammography device according to an exemplary embodiment of the present invention as described above, at the time of pressing the object to be inspected by the pressing pad, pressing for a portion at which relatively small pain is felt and a portion at which relatively large pain is felt is changed, that is, pressing force is concentrated on the portion at which the small pain is felt and the portion at which the large pain is felt is slowly pressed, thereby making it possible to remove or minimize pain or discomfort applied to a subject.

Further, since X-ray photographing may be performed in this comfortable state, a high photographing accuracy may be accomplished, such that the number of times of unnecessary photographing is decreased, thereby making it possible to decrease exposure to X-ray.

DESCRIPTION OF DRAWINGS

FIG. 1 is a perspective view illustrating an entire configuration of a mammography device according to an exemplary embodiment of the present invention.

FIG. 2A is a plan view of an example of a pressing pad and a pressing pad support part configuring the mammography device according to an exemplary embodiment of the present invention.

FIG. 2B is a cross-sectional view of the pressing pad and the pressing pad support part taken along line B-B of FIG. 2A.

FIG. 3 is a plan view of another example of a pressing pad and a pressing pad support part configuring the mammography device according to an exemplary embodiment of the present invention.

FIGS. 4A to 4C are schematic views illustrating a process of pressing an object to be inspected by the mammography device according to an exemplary embodiment of the present invention.

FIG. 5 is a side view illustrating a modified example of a pressing pad that may be used in the mammography device according to an exemplary embodiment of the present invention.

FIG. 6 is a view illustrating various kinds of twisting springs that may be used in the mammography device according to an exemplary embodiment of the present invention.

BEST MODE

Additional objects, features, and advantages of the present invention may be more clearly understood from the following detailed description and the accompanying drawings. Prior to a detailed description of the present invention, the present invention may be variously modified and altered and have several exemplary embodiments. Examples described below and illustrated in the drawings are not to limit the present invention to specific exemplary embodiments. In addition, various modifications, alterations, and amendments may be made in the scope of the following claims, and it may be understood that these modifications, alterations, and amendments fall within the scope of the present invention.

It is to be understood that when one element is referred to as being "connected to" or "coupled to" another element, it may be connected directly to or coupled directly to another element or be connected indirectly to or coupled indirectly to another element with the other element intervening therebetween. On the other hand, it is to be understood that when one element is referred to as being "connected directly to" or "coupled directly to" another element, it may be connected to or coupled to another element without the other element intervening therebetween.

Terms used in the present specification are used only in order to describe specific exemplary embodiments rather than limiting the present invention. Singular forms include plural forms unless the context clearly indicates otherwise.

It will be further understood that terms "include", "have", or the like, used in the present specification are to specify the presence of features, numerals, steps, operations, components, parts mentioned in the present specification, or a combination thereof, but do not preclude the presence or addition of one or more other features, numerals, steps, operations, components, parts, or a combination thereof.

A term "part", "-er/or", "unit", "module", or the like, described in the present specification means a processing unit of at least one function or operation and may be implemented by hardware or software or a combination of hardware and software.

In describing the present invention with reference to the accompanying drawings, the same components will be denoted by the same reference numerals, and an overlapped description therefor will be omitted. When it is decided that a detailed description for the known art related to the present invention may unnecessarily obscure the gist of the present invention, the detailed description will be omitted.

Hereinafter, a digital mammography device according to an exemplary embodiment of the present invention will be described in detail with reference to the accompanying drawings. Although a digital type mammography device has been described as an example of a "mammography device" in the present specification, the present invention is not limited thereto, but may also be applied to an analog type mammography device.

Referring to FIG. 1, which is a perspective view illustrating an entire configuration of a mammography device according to an exemplary embodiment of the present invention, the mammography device according to an exemplary embodiment of the present invention is configured to include a device body 100 including basic components for X-ray photographing and a support column 200 to which the device body 100 is connected to be vertically movable. The support column 200, which is a support having a lower end portion fixed to a bottom and having a vertical column shape, provides a vertical axis to the device body 100 so that the device body 100 may ascend or descend in a vertical length direction.

The device body 100 has an arc shape in which upper and lower (both) end portions thereof face each other, and is called a C-arm since it generally has a C-shape or a shape similar to the C-shape. The device body 100 includes a column connection part 110 connected to the support column 200 so as to ascend or descend in the vertical direction and a vertical connection part 120 connected to the column connection part 110 so as to be rotatable with respect to the column connection part 110. The device body 100 includes a generator 130 mounted at one end portion (for example, an upper end portion in the present exemplary embodiment) of the vertical connection part 120 of the device body 100 and irradiating an X-ray toward the other end portion (for example, a lower end portion in the present exemplary embodiment) of the vertical connection part 120 facing one end portion of the vertical 15 connection part 120, a detector 140 mounted at the other end portion of the vertical connection part 120 and facing the generator 130, and a pressing pad 150 linearly reciprocating between the generator 130 and the detector 140 along an inner surface of the device body 100 and having a plate shape. Here, the pressing pad 150 is provided with a pain alleviating means for alleviating pain when the pressing pad 150 presses an object to be inspected. The pain alleviating means will be again described in more detail below.

Meanwhile, the object to be inspected is positioned between the pressing pad 150 and the detector 140, and X-ray photographing is performed on the object to be inspected. Alternatively, an inspection plate 160 may be selectively installed between the pressing pad 150 and the detector 140, the object to be inspected may be positioned between the pressing pad 150 and the inspection plate 160, and X-ray photographing may be performed on the object to be inspected. That is, in the case in which the inspection plate 160 is not present, the detector 140 serves as a support part for the object to be inspected, and in the case in which the inspection plate 160 is present, the inspection plate 160 serves as a support part for the object to be inspected.

The vertical connection part 120 is connected to the column connection part 110 so as to be rotatable with respect to a horizontal axis so that a breast may be photographed by a mediolateral oblique view, and a rotation driving part (not illustrated) for rotating the vertical connection part 120 as described above is installed at the column connection part 110.

The vertical connection part 120 basically includes upper and lower (both) end portions at which the generator 130 and the detector 140 are mounted, respectively, and a column connecting the upper and lower (both) end portions to each other. A pressing pad support part 152 to which the pressing pad 150 is connected is slidably mounted on the column of the vertical connection part 120, and a driving means for vertically moving the pressing pad support part 152 is installed at one side of the vertical connection part 120. The breast positioned on the detector 140 or on the inspection plate 160 in some cases is pressed by the above-mentioned vertical movement of the pressing pad support part 152 and the pressing pad 150 connected to the pressing pad support part 152.

The generator 130 mounted at an upper end portion of the device body 100 is a device allowing electrons having high kinetic energy to collide with a metal target to generate an X-ray, and preferably includes an optical system such as a collimator, or the like, controlling an irradiation direction or an irradiation area of the X-ray.

The detector 140 mounted at a lower end portion of the device body 100 basically is a means for receiving the X-ray passing through the breast to obtain an image, and since the breast is put on the detector 140, the detector 140 may also serve as the support part for the object to be inspected for supporting the breast. That is, the breast is put on the detector 140 and is then pressed by the pressing pad 150, such that the breast is pressed between the detector 140 and the pressing pad 150, and the breast in a state in which it is pressed as described above is photographed by the generator 130 and the detector 140. The detector 140 generates an electric signal for each position that is in proportion to an amount of incident X-ray, and reads the electrical signal and position information and processes the read electrical signal and position information by an image processing algorithm, thereby making it possible to obtain an X-ray image of the breast. Here, a general technology content such as a direct converting scheme of obtaining the electrical signal directly from the X-ray without having a separate intermediate step, an indirect converting scheme of obtaining the electrical signal indirectly by a visible ray converted from the X-ray, or the like, depending on a scheme of converting the X-ray may be widely applied to the detector 140.

The inspection plate 160 may be included as a selective component in order to substitute for a function of the detector 140 as the support part for the object to be inspected. In the case in which the inspection plate 160 is included, the breast is pressed by the pressing pad 150 and the inspection plate 160, and the breast in this state is photographed by the generator 130 and the detector 140. Therefore, the detector 140 performs only a function of receiving the X-ray passing through the breast to obtain the image.

Next, an example of a pain alleviating means for alleviating a pressing level of the object to be inspected will be described with reference to FIGS. 2A and 2B. FIG. 2A is a plan view of an example of a pressing pad 150 and a pressing pad support part 152 including the pain alleviating means configuring the mammography device according to an exemplary embodiment of the present invention, and FIG. 2B is a cross-sectional view of the pressing pad and the pressing pad support part taken along line B-B of FIG. 2A.

Basically, the pain alleviating means of the present invention is to press the object to be inspected while changing a gradient of the pressing pad 150 from a pressing initial state in which pressing is not applied to the object to be inspected to a pressing completion state for X-ray photographing. That is, at the time of pressing the object to be inspected by the pressing pad 150, a proximal portion (a portion adjacent to a chest) of the object to be inspected at which relatively small pain is felt may be pressed from an early stage, and a distal portion (a portion adjacent to a nipple) of the object to be inspected at which slightly large pain is felt may be slowly pressed from a later stage.

In detail, the pressing pad 150 and the pressing pad support part 152 are connected to each other so as to be rotatably with respect to each other through a hinge shaft 151 of the pressing pad 150 in a width direction. To this end, the pressing pad 150 includes hinge shaft installation parts 150a protruding downwardly on a lower surface thereof, as illustrated in FIG. 2B. One hinge shaft installation part 150a is formed at each of both side portions of the pressing pad 150 in the width direction. That is, two hinge shaft installation parts 150a are formed. In detail, the hinge shaft installation parts 150a are formed at both side portions of the pressing pad 150 in the width direction at a position spaced apart from a central portion of the pressing pad 150 toward the pressing pad support pad 152 by a predetermined distance. In addition, the pressing pad support part 152 includes a first part 152a having one end connected to the vertical connection part 120 and second parts 152b branched as two branches from the other end of the first part 152a. Front end portions of the second parts 152b branched as the two branches are connected, respectively, to the hinge shaft installation parts 150a of the pressing pad 150 through the hinge shaft 151. Therefore, the pressing pad 150 having the plate shape is connected to the pressing pad support part 152 so as to be rotatable with respect to the pressing pad support part 152 above the pressing pad support part 152.

Pad side support jaws 150b are formed at a rear end portion of the pressing pad 150 toward the pressing pad support part 152. The pad side support jaws 150b protrude at both side surfaces of the pressing pad 150 in the width direction at the rear end portion of the pressing pad 150. Particularly, the pad side support jaws 150b contact the second parts 152b of the pressing pad support part 152 at a position at which the pressing pad 150 is in parallel with the support part for the object to be inspected. The pad side support jaws 150b may serve as a stopper, as described below. In addition, support part side support jaws 152bc having a recess shape are formed at positions corresponding to the pad side support jaws 150b on an upper surface of the second part 152b of the pressing pad support part 152. Coil springs 154 are interposed as elastic means between the pad side support jaws 150b and the support part side support jaw 152bc.

The pressing pad 150 has stoppers 150c protruding on both side surfaces thereof in the width direction at positions facing the pad side support jaws 150b with the hinge shaft 151 interposed therebetween. Here, the stoppers 150c may contact the front end portions of the second parts 152b of the pressing pad support part 152. The stoppers 150c serve to limit an inclination angle of a pressing initial state.

In the configuration as described above, the pressing pad 150 is maintained in a state in which a front end portion thereof adjacent to a subject is inclined toward the object to be inspected, that is, a state in which the front end portion is inclined downwardly, in a pressing initial state that does not have a load, that is, a state in which pressing is not applied to the object to be inspected, by the coil springs 154 and the stoppers 150c. In the pressing initial state, an inclination angle of the pressing pad 150 may be determined by a position, a thickness, and the like, of the stopper 150c. That is, in the pressing initial state, the pressing pad 150 tends to rotate in a clockwise direction around the hinge shaft 151 in FIG. 2B by elastic force of the coil springs 154 interposed between the pad side support jaws 150b and the support part side support jaws 152bc. However, in a predetermined rotation state, the stoppers 150c of the pressing pad 150 contact the front end portions of the second parts 152b of the pressing pad support part 152 to limit rotation of the pressing pad 150 such that an inclination angle of the pressing pad 150 in the pressing initial state is maintained.

In addition, when the pressing of the object to be inspected is performed by the pressing pad 150, the pressing pad 150 rotates in a counterclockwise direction around the hinge shaft 151 in FIG. 2B by repulsive force transferred from the object to be inspected. The pad side support jaws 150b of the pressing pad 150 contact the second parts 152b of the pressing pad support part 152 by the above-mentioned rotation, such that rotation of the pressing pad 150 to a position that is in parallel with the support part for the object to be inspected is limited.

An initial inclination position and a final position of the pressing pad 150 as described above are determined by positions at which the stoppers 150c and the pad side support jaws 150b of the pressing pad 150 contact the pressing pad support part 152, but initial/final lengths of the coil springs 154, an elastic modulus, and the like, need to be considered at the time of determining the initial inclination position and the final position of the pressing pad 150.

Another modified example of the pressing pad 150 and the pressing pad support part 152 to which a pain alleviating means is applied is illustrated in FIG. 3. In the modified example illustrated in FIG. 3, the pad side support jaws 150b may protrude at the center of the rear end portion of the pressing pad 150. Here, the support part side support jaws 152bc having a recess shape, which is the same as the shape illustrated in FIG. 2B, are formed on an upper surface of the second part 152b of the pressing pad support part 152 at positions corresponding to the pad side support jaws 150b. Other components such as the coil springs 154 interposed between the pad side support jaws 150b and the support part side support jaws 152bc, the stoppers 150c, and the like, are substantially the same as those of an example illustrated in FIGS. 2A and 2B. As another example, a twisting spring (See FIGS. 4A to 4C) may also be mounted on the hinge shaft 151, instead of the coil spring 154 without forming the support part side support jaws 152bc on the pressing pad support part 152. An operation of these examples is the same as that of the example illustrated in FIGS. 2A and 2B.

In addition, it may be easily understood by those skilled in the art that other components allowing the front end portion of the pressing pad 150 to be inclined downwardly in the pressing initial state and allowing the pressing pad 150 to be positioned in parallel with the support part for the object to be inspected in the pressing completion state may be implemented in other several forms other than the example and the modified example described above.

Next, a process of pressing an object to be inspected by the mammography device according to an exemplary embodiment of the present invention will be described with reference to FIGS. 4A to 4C. In FIGS. 4A and 4C, components such as the coil springs 154, the pad side support jaws 150b and the support part side support jaws 152bc, the stoppers 150c, and the like, described in FIGS. 2A and 2B have been omitted so that operations of main parts clearly appear.

First, FIG. 4A illustrates a pressing initial state in which a breast BR, which is an object to be inspected, is put on the detector 140 (or the inspection plate 160 in the case in which the inspection plate 160 is present) and the pressing pad 150 descends to start to contact the object BR to be inspected. In this state, the front end portion of the pressing pad 150 toward the breast BR is inclined downwardly due to the coil springs 154 interposed between the pad side support jaws 150b and the support part side support jaws 152bc. In a state in which the front end portion of the pressing pad 150 is inclined as described above, the front end portion of the pressing pad 150 contacts the proximal portion (the portion adjacent to the chest) of the breast BR.

Then, as illustrated in FIG. 4B, when the pressing pad 150 descends to perform pressing on the breast BR, the pressing pad 150 rotates in the counterclockwise direction around the hinge shaft 151 as illustrated by an arrow in FIG. 4B by repulsive force transferred from the breast BR. In this case, a contact surface between the pressing pad 150 and the breast BR is gradually increased from the proximal portion of the breast BR to the distal portion (the portion adjacent to the nipple) of the breast BR.

As illustrated in FIG. 4C, when the pressing pad 150 descends up to a pressing completion state, the pad side support jaws 150b of the pressing pad 150 contact the second parts 152b of the pressing pad support part 152, such that the pressing pad 150 is positioned in parallel with the support part for the object to be inspected. In this case, a contact surface between the pressing pad 150 and the breast BR is maximally increased, such that the pressing pad 150 becomes a state in which a desired X-ray image may be obtained. The pressing pad 150 may also descend up to the pressing completion state in a state in which it is positioned in parallel with the support part for the object to be inspected before it arrives at the pressing completion state, depending on an elastic modulus of the coil springs 154.

As described above, since the gradient of the pressing pad 150 is changed during a period in which the pressing pad 150 presses the breast BR, the proximal portion (the portion adjacent to the chest) of the breast BR at which pain is relatively small first starts to be pressed (see FIG. 4A), such that pressing force is concentrated on the proximal portion (during an entire pressing process), while the distal portion (the portion adjacent to the nipple) of the breast BR at which pain is relatively large is slowly pressed after a pressing process is performed to some degrees. Therefore, a pressing level at the portion (the portion adjacent to the nipple) at which the pain is large may be significantly alleviated, such that pain of the subject may be decreased.

According to the above-mentioned configuration, since the front end portion of the pressing pad 150 contacts the proximal portion (the portion adjacent to the chest) of the breast BR in the pressing initial state, when an angle is formed at an edge of the front end portion of the pressing pad 150, pain of the subject may be caused. Therefore, the front end portion of the pressing pad 150 has a round shape as illustrated in FIGS. 2B and 4A to 4C, such that the pain that may be caused by the front end portion of the pressing pad 150 in the pressing initial state of the breast may be removed. Although rounds are formed at both of upper and lower edges of the front end portion of the pressing pad 150 in FIGS. 2B and 4A to 4C, the round may also be formed at only the lower edge contacting the object to be inspected.

On the other hand, when the front end portion of the pressing pad 150 has a shape in which it is bent upwardly as illustrated in FIG. 5, the pain that may be caused by the front end portion of the pressing pad 150 in the pressing initial state of the breast may be removed. The round shape and the bent shape may also be similarly applied to the detector 140 (or the inspection plate 160).

Although the examples of the pressing pad 150 and the pressing pad support part 152 have been described hereinabove, the present invention is not limited thereto. For example, the present invention may be implemented by configuring the support part (the detector 140 or the inspection plate 160) for the object to be inspected so as to be rotatable with respect to the device body 100 and elastically deflecting the front end portion of the support part for the object to be inspected adjacent to the subject so as to be inclined upwardly toward the object to be inspected in the pressing initial state. Also in this case, it is preferable that when the pressing is completed, the support part (the detector 140 or the inspection plate 160) for the object to be inspected is in parallel with the pressing pad 150. In addition, the pain alleviating means according to the present invention may also be applied to both of the pressing pad 150 and the support part for the object to be inspected.

It will be obvious to those skilled in the art to which the present invention pertains that the present invention described above is not limited to the above-mentioned exemplary embodiments and the accompanying drawings, but may be variously substituted, modified, and altered without departing from the scope and spirit of the present invention.

The invention claimed is:

1. A mammography device comprising:
   a generator irradiating an X-ray;
   a support part for an object to be inspected including a detector positioned to face the generator; and
   a pressing pad and a pressing pad support part moving between the generator and the support part for an object to be inspected to press the object to be inspected,
   wherein in a pressing initial state of the object to be inspected, the pressing pad is configured so that a front end portion of the pressing pad toward a subject is elastically deflected to a position inclined toward the object to be inspected, and wherein the pressing pad is rotatably connected to the pressing pad support part; and
   stoppers protruding in a width direction from the pressing pad and limiting an inclination angle of the pressing pad in the pressing initial state by contacting front end portions of the pressing pad support part.

2. The mammography device of claim 1, wherein in a pressing completion state of the object to be inspected, the support part for the object to be inspected and the pressing pad are configured in parallel with each other, except that the front end portion of the pressing pad is bent away from the support part.

3. The mammography device according to claim 2, further comprising:
- an elastic member providing elasticity to at least one of the support part for an object to be inspected and the pressing pad that is rotatably installed when at least one of the support part for an object to be inspected and the pressing pad that is rotatably installed rotates between the inclined position in the pressing initial state of the object to be inspected and the parallel position in the pressing completion state of the object to be inspected; and
- pad side support jaws formed at a rear portion of the pressing pad and limiting an angle of rotation in the parallel position by contacting portions of the pressing pad support part.

4. The mammography device according to claim 3, wherein the elastic member comprises:
- a hinge shaft rotatably connecting the pressing pad to the pressing pad support part; and
- at least one of a coil spring interposed between the pressing pad and the pressing pad support part, and a twisting spring installed on the hinge shaft.

5. The mammography device according to claim 3, wherein the pad side support jaws protrude from side surfaces of the pressing pad and limit the angle of rotation in the parallel position by contacting portions of the pressing pad support part.

6. The mammography device according to claim 3, wherein the pad side support jaws protrude from a center of a rear end portion of the pressing pad and limit the angle of rotation in the parallel position by contacting portions of the pressing pad support part.

7. The mammography device according to claim 1, wherein at least one of the front end portion of the pressing pad and a front end portion of the support part has a round shape at at least an edge thereof contacting the object to be inspected.

8. The mammography device according to claim 1, further comprising:
- a support column;
- a column connection part connected to the support column;
- a vertical connection part on which the generator, the support part, and the pressing pad are mounted, wherein the vertical connection part is rotatably connected to the column connection part.

* * * * *